United States Patent
Li et al.

(10) Patent No.: US 8,135,249 B2
(45) Date of Patent: *Mar. 13, 2012

(54) FIBER SPECTROSCOPIC PROBE MOUNTABLE ON A MICROSCOPE

(75) Inventors: Qingxiong Li, Newark, DE (US); Ryan Edward Sullivan, Yardley, PA (US); Xin Jack Zhou, Hockessin, DE (US); Sean Xiaolu Wang, Wilmington, DE (US)

(73) Assignee: BWT Property, Inc., Newark, DE (US)

( * ) Notice: Subject to any disclaimer, the term of this patent is extended or adjusted under 35 U.S.C. 154(b) by 151 days.

This patent is subject to a terminal disclaimer.

(21) Appl. No.: 12/611,138

(22) Filed: Nov. 3, 2009

(65) Prior Publication Data

US 2011/0081111 A1    Apr. 7, 2011

Related U.S. Application Data

(63) Continuation-in-part of application No. 12/573,278, filed on Oct. 5, 2009.

(51) Int. Cl.
*G02B 6/32* (2006.01)
*G02B 6/26* (2006.01)
*G01J 3/44* (2006.01)

(52) U.S. Cl. ............................ 385/33; 385/31; 356/301

(58) Field of Classification Search ................. 385/31, 385/33, 116, 12, 34, 27; 356/12, 301; 436/46, 436/514
See application file for complete search history.

(56) References Cited

U.S. PATENT DOCUMENTS

| | | | |
|---|---|---|---|
| 5,194,912 A | 3/1993 | Batchelder et al. | 356/301 |
| 6,038,363 A * | 3/2000 | Slater et al. | 385/147 |
| 6,353,476 B1 * | 3/2002 | Allen et al. | 356/301 |
| 6,687,000 B1 * | 2/2004 | White | 356/328 |
| 7,102,746 B2 | 9/2006 | Zhao | 356/301 |
| 7,327,444 B2 * | 2/2008 | Naka et al. | 356/73 |
| 7,403,281 B2 | 7/2008 | Carron et al. | 356/301 |
| 2005/0128476 A1 * | 6/2005 | Zhao | 356/301 |
| 2006/0038980 A1 * | 2/2006 | Naka et al. | 356/73 |
| 2006/0114459 A1 * | 6/2006 | Aikawa | 356/328 |
| 2011/0081110 A1 * | 4/2011 | Sullivan et al. | 385/31 |
| 2011/0081111 A1 * | 4/2011 | Li et al. | 385/33 |

* cited by examiner

*Primary Examiner* — Brian Healy

(57) ABSTRACT

A fiber spectroscopic probe that can be mounted directly above the objective lens of a standard microscope to add a spectroscopic function to the microscope. The constructed microscope with fiber spectroscopic probe is suitable for micro-sampling, Raman analysis, as well as fluorescence analysis and can be easily reconfigured for different excitation/detection wavelengths. The fiber spectroscopic probe only consists of a minimum number of optical components and is compact enough to induce minimum alteration to the optical path of the microscope.

14 Claims, 4 Drawing Sheets

FIBER SPECTROSCOPIC PROBE MOUNTABLE ON A MICROSCOPE

REFERENCE TO RELATED APPLICATION

This application is a continuation-in-part of U.S. application Ser. No. 12/573,278, entitled "FIBER SPECTROSCOPIC PROBE MOUNTABLE ON A MICROSCOPE", filed on Oct. 5, 2009, by Ryan E. Sullivan, Qingxiong Li, Xin J. Zhou, and Sean X. Wang. The subject matter of the above mentioned U.S. applications is hereby incorporated herein by reference in its entirety.

FIELD OF THE INVENTION

This invention generally relates to a fiber spectroscopic probe, and more specifically to a fiber spectroscopic probe mountable on a microscope.

BACKGROUND

Raman microscopy is a useful spectroscopic technique that permits nondestructive, spatially resolved measurements within the samples. Conventional Raman microscopes such as those disclosed in U.S. Pat. No. 5,194,912 to Batchelder et al. suffer from bulky sizes, which limits them only to laboratory usages. Recently, with the development of diode lasers as the excitation light source, Raman spectrometers were made as compact attachments that can be mounted onto a standard microscope to convert it into a Raman microscope. Some exemplary apparatus can be found in U.S. Pat. No. 7,102,746 to Zhao and U.S. Pat. No. 7,403,281 to Carron et al., which are hereby incorporated herein as references. Yet the large number of optical components in a Raman spectrometer still places a lower limit on its physical size. As a result, the incorporation of the Raman spectrometer inevitably alters the optical path length of the microscope. Certain modifications have to be made to the microscope to accommodate the Raman spectrometer, which may disturb the microscope's originally designed functions.

There thus exists a need for an improved spectroscopic accessory that can be mounted onto a standard microscope to add a spectroscopic function to the microscope and in the meantime induces minimum alteration to the optical path of the microscope.

SUMMARY OF THE INVENTION

It is the overall goal of the present invention to solve the above mentioned problems and provide a fiber spectroscopic probe that can be mounted directly above the objective lens of a standard microscope to add a spectroscopic function to the microscope. The constructed microscope with fiber spectroscopic probe is suitable for micro-sampling, Raman analysis, as well as fluorescence analysis and can be easily reconfigured for different excitation/detection wavelengths. The fiber spectroscopic probe only consists of a minimum number of optical components and is compact enough to induce minimum alteration to the optical path of the microscope.

BRIEF DESCRIPTION OF THE FIGURES

The accompanying figures, where like reference numerals refer to identical or functionally similar elements throughout the separate views and which together with the detailed description below are incorporated in and form part of the specification, serve to further illustrate various embodiments and to explain various principles and advantages all in accordance with the present invention.

Figure 1:
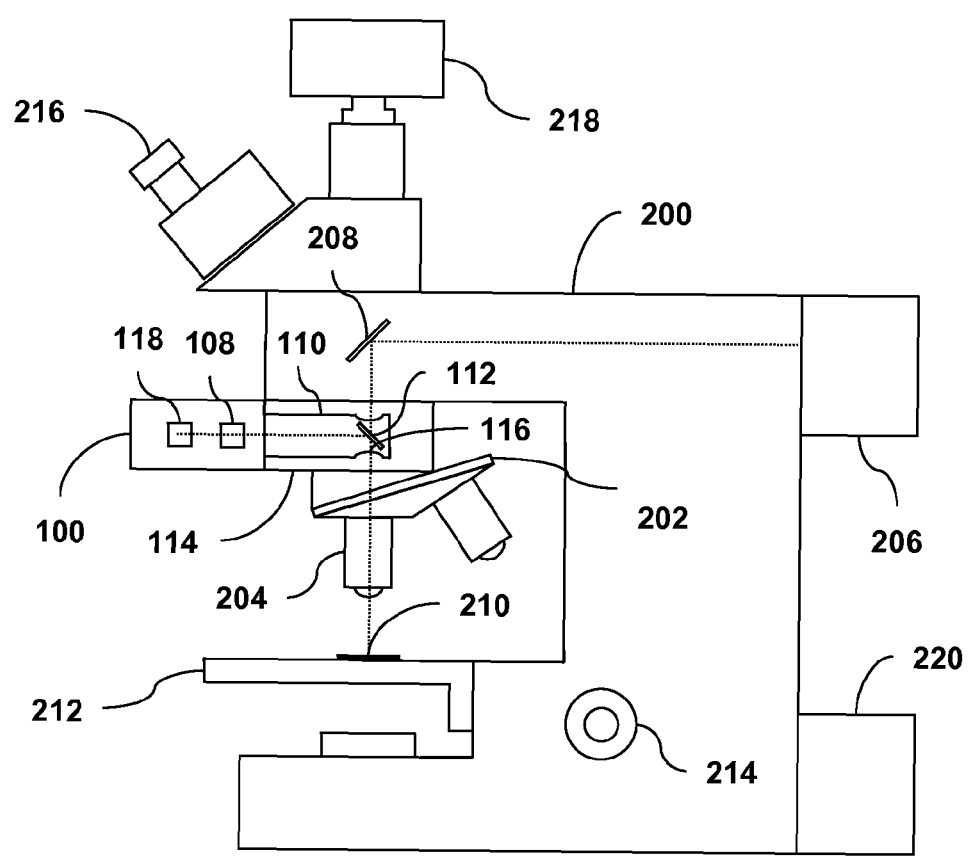
FIG. 1 is a schematic side view of a first exemplary embodiment of the fiber spectroscopic probe that is mounted on a microscope.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION

Before describing in detail embodiments that are in accordance with the present invention, it should be observed that the embodiments reside primarily in combinations of method steps and apparatus components related to a fiber spectroscopic probe mountable on a microscope. Accordingly, the apparatus components and method steps have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

In this document, relational terms such as first and second, top and bottom, and the like may be used solely to distinguish one entity or action from another entity or action without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

Figure 2:
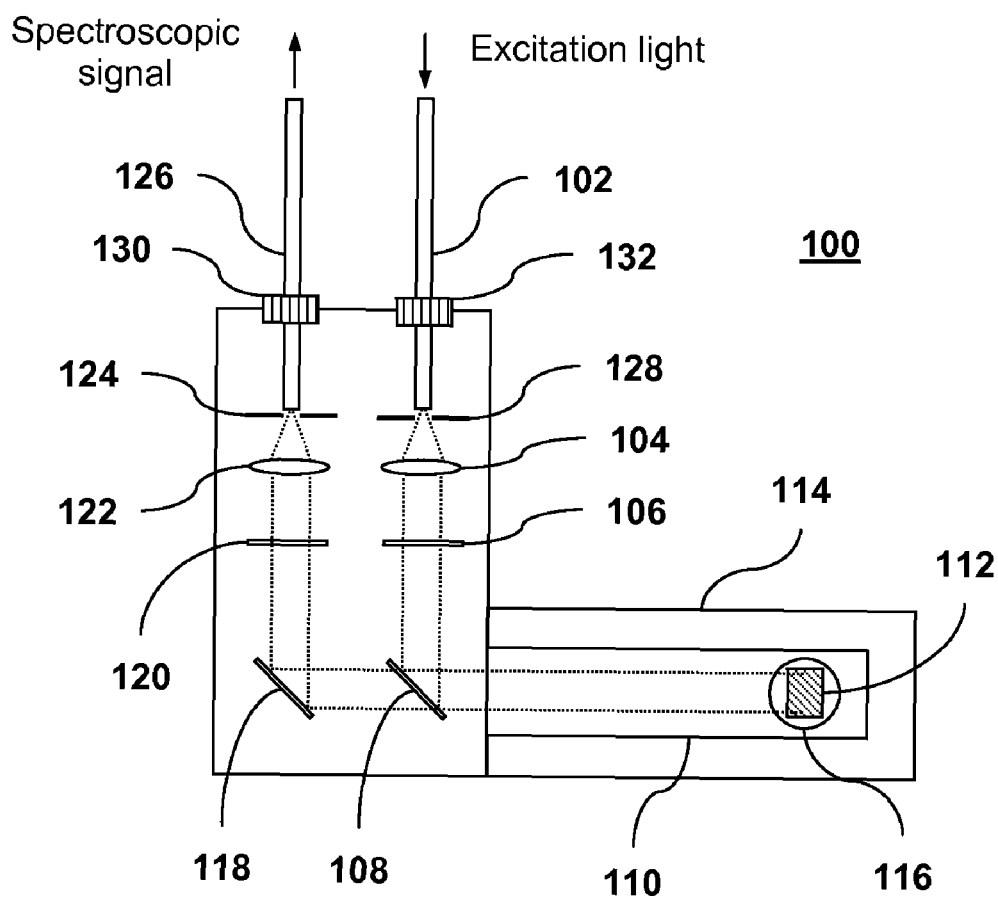
FIG. 2 is a schematic top view of the fiber spectroscopic probe of FIG. 1.

FIG. 1 and FIG. 2 show a schematic side view and a schematic top view of a first exemplary embodiment of the fiber spectroscopic probe, respectively. In this exemplary embodiment, the fiber spectroscopic probe 100 is a fiber Raman probe, which can be mounted onto a standard microscope 200 to convert it into a Raman microscope.

Referring to FIG. 1, the microscope 200 is a standard light microscope comprising the following components: an epi-illumination light source 206 and a trans-illumination light source 220 for providing illumination, a stage 212 for holding the sample 210, a nosepiece 202 and a plurality of objective lenses 204 for collecting the reflected or transmitted light from the sample, as well as an eyepiece 216 and a camera 218 as the viewing device. The epi-illumination light produced by the light source 206 is reflected by a beam splitter 208 (preferably a half-silvered mirror) into the main optical path of the microscope. The focus of the microscope can be adjusted though a knob 214.

Referring to FIG. 1 and FIG. 2, the fiber Raman probe 100 comprises an input optical fiber 102 for delivering excitation light from a laser light source (not shown). The laser light from the input optical fiber 102 is collimated by an optical lens 104 and transmits through a band-pass optical filter 106 to remove the out-of-band background noise. The filtered laser light is then reflected by a dichroic beam splitter 108 to be directed toward an output tube 110. The output tube 110 is enclosed in an adapter member 114 to be mounted onto the microscope 200 in a position directly on top of the nosepiece 202 and the objective lens 204. The distal end of the output tube 110 comprises two transparent windows (or two openings) 116 and a 45° dichroic beam splitter 112. The dichroic beam splitter 112 is transmissive to the wavelengths of the illumination light and reflective to the wavelengths longer than that of the laser light such that the laser light is reflected towards the objective lens 204 to be focused onto the sample 210. Here the laser light shares the same optical path as the illumination light of the microscope. The laser light excites a Raman scattered light (a spectroscopic signal) from the sample 210, which is collected by the objective lens 204 and then reflected by the dichroic beam splitter 112 into the output tube 110. The Raman scattered light transmits through the dichroic beam splitter 108 to be reflected by a mirror 118 and directed toward a long-pass optical filter 120 and an optical lens 122. The long-pass optical filter 120 acts as a Rayleigh rejection filter to remove the Rayleigh scattered light from the Raman scattered light. The optical lens 122 then focuses the Raman scattered light into an output optical fiber 126 to be transmitted to a spectrometer device (not shown) for spectrum analysis. In this exemplary embodiment, the laser light source is preferably a diode laser with its output wavelength in the near infrared (NIR) region. The dichroic beam splitter 108 has a cut-off wavelength near the laser wavelength to reflect the laser light and in the meantime transmit the Raman scattered light at longer wavelengths. The fiber Raman probe 100 may further comprise two fiber adapters 130 and 132, which allow the user to change the types of output and input optical fibers in accordance to the spectrometer device and the laser light source that are used. For example, the user may choose a single mode laser as the light source and a single mode fiber as the input optical fiber such that the laser light can be focused to a small spot size on the sample to increase the spatial resolution of the Raman microscope. The user may also select a multimode laser light source and a multimode input optical fiber so that the power of the excitation light can be increased to enhance the intensity of the Raman scattering signal.

Both the input optical fiber 102 and the output optical fiber 126 of the fiber Raman probe 100 have a limited optical aperture of less than a few hundred microns (less than a few microns for single mode fiber). Thus the excitation light can be focused to a small spot size on the sample. In the meantime, the output optical fiber 126 will reject most of the out-of-focus light from the sample. This spatial filtering effect adds a confocal feature to the constructed Raman microscope and allows it to examine a series of sections of the sample at different depths. Two spatial pinholes 124 and 128 (either fixed or adjustable) can be inserted in front of the input end of the output optical fiber 126 and the output end of the input optical fiber 102, respectively to provide further control of their optical apertures such that this 'confocal' spatial filtering effect can be further enhanced.

The fiber Raman probe 100 contains only a minimum number of optical components. As a result, its thickness can be made very small (e.g. <1 cm) so that the incorporation of the fiber Raman probe only induces a minimum alteration to the optical path length of the microscope. This brings in several advantages. First, the fiber Raman probe 100 can be mounted directly above the nosepiece 202 and the objective lens 204 of the microscope, where the light beam exhibits the smallest spot size in the optical path. Thus the Raman scattered light from the sample can be effectively collected by the fiber Raman probe and in the meantime, the reflected (epi-illumination mode) or transmitted (trans-illumination mode) visible light from the sample 210 will not be blocked. Second, the illumination condition of the microscope (such as Kohler illumination in the epi-illumination mode) will not be disturbed by the incorporation of the fiber Raman probe. Third, the fiber Raman probe does not occupy any viewing port of the microscope hence not affecting its normal viewing function.

With some minor modifications to its optical components, the same fiber probe 100 can be used for other spectroscopic applications as well. For example, by replacing the NIR laser light source with an ultraviolet (UV) or visible light source and adjusting the spectral property of the optical components correspondingly, the fiber probe can convert a standard microscope into a fluorescence microscope for examining the fluorescence or phosphorescence property of the samples.

Figure 3:
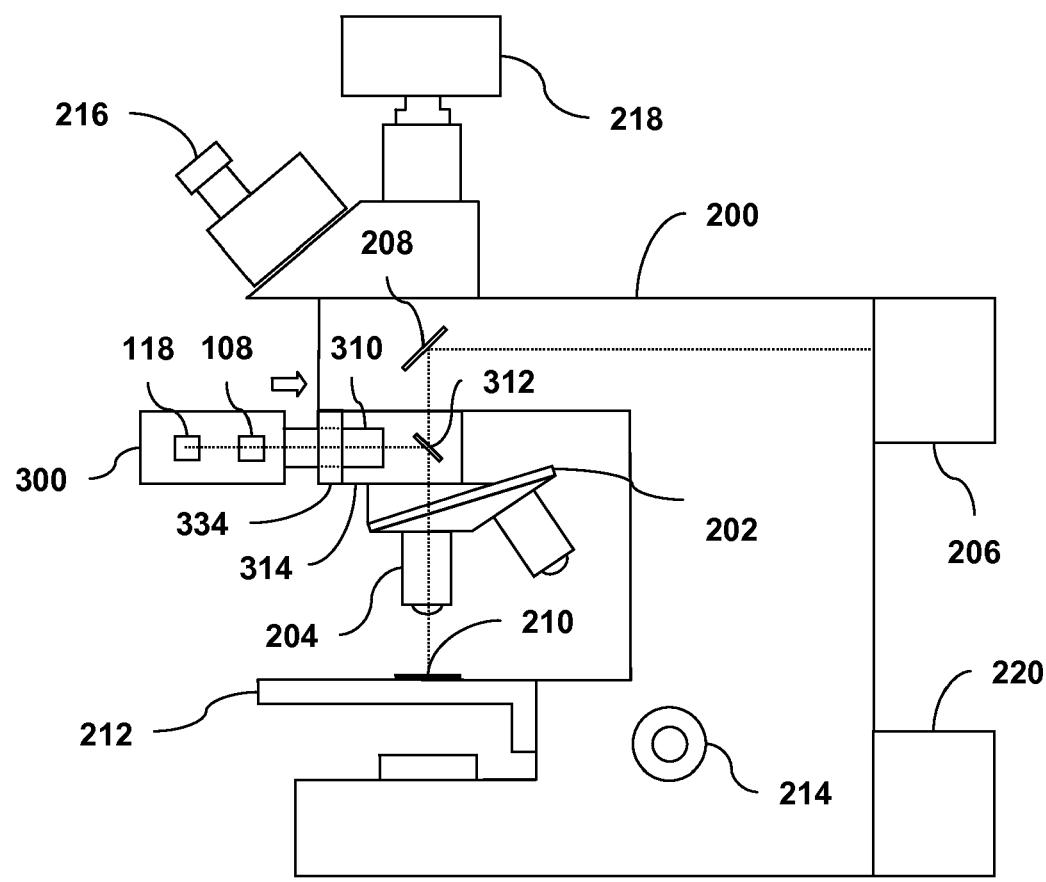
FIG. 3 is a schematic side view of a second exemplary embodiment of the fiber spectroscopic probe that is mounted on a microscope.
Figure 4:
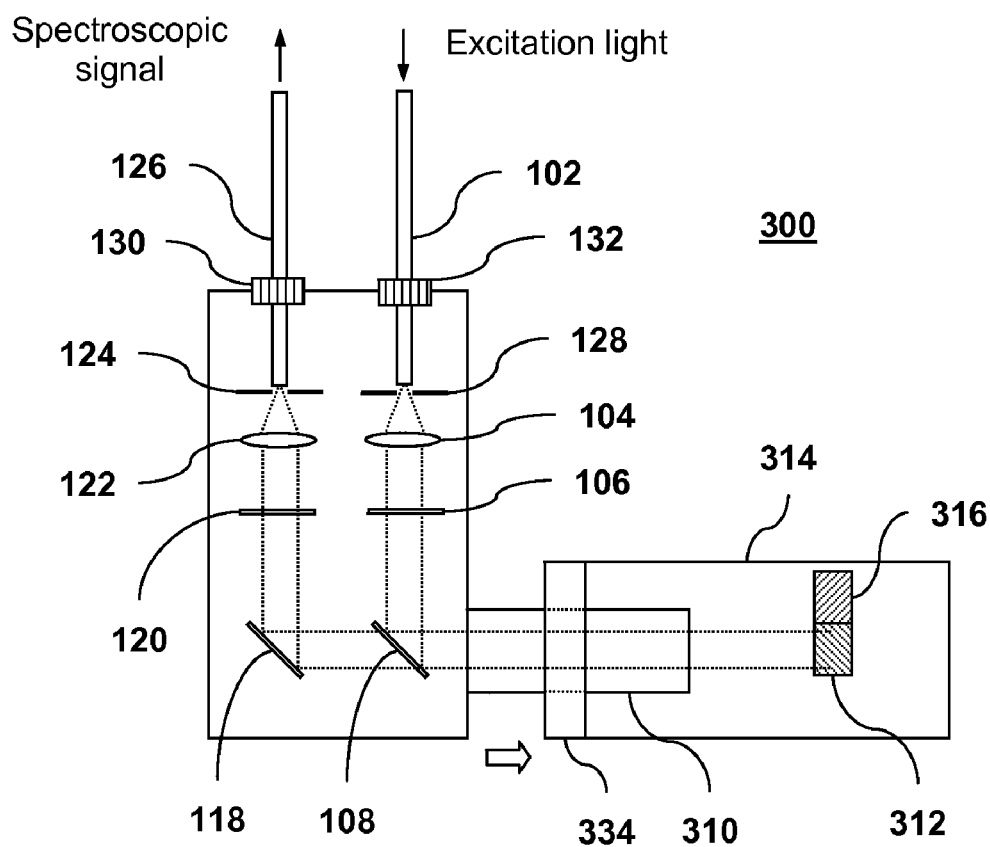
FIG. 4 is a schematic top view of the fiber spectroscopic probe of FIG. 3.

FIG. 3 and FIG. 4 show a schematic side view and a schematic top view of a second exemplary embodiment of the fiber spectroscopic probe, respectively. The fiber spectroscopic probe 300 has a similar structure as does the fiber Raman probe 100 of FIG. 1 and FIG. 2 except that the adapter member 314 is detachable from the spectroscopic probe. The adapter member 314 has a receptacle 334 to secure the output tube 310 of the spectroscopic probe and mount the spectroscopic probe on top of the nosepiece 202 and the objective lens 204 of the microscope 200. This configuration allows the user to switch between different types of fiber spectroscopic probes without changing the adaptor member, which ensures the alignment of the output optical path of the spectroscopic probe with that of the microscope. In addition, the adaptor member 314 may comprise two or more switchable dichroic beam splitters 312 and 316 at different operating wavelengths such that the user may select a set of excitation/detection wavelengths. For example, the user may switch between a 532 nm fiber Raman probe and a 785 nm fiber Raman probe by simply switching the dichroic beam splitter of the adapter member 314. This reconfiguration capability allows the user to select the optimum excitation/detection wavelength according to the type of sample to be measured. Alternatively, the adaptor member 314 may comprise a multiband beam splitter (not shown), which has multiple reflection bands at different wavelengths to be used for different excitation/detection wavelengths.

In a slight variation of the previous disclosed embodiments, the dichroic beam splitter 112 in FIG. 2 or 312 and 316 in FIG. 4 is replaced with an optical mirror. The optical mirror has a physical size comparable to the beam size of the laser light yet smaller than the beam size of the illumination light such that only a portion of the reflected (epi-illumination mode) or transmitted (trans-illumination mode) illumination light from the sample will be blocked. Thus the normal viewing function of the microscope is not disturbed by the incorporation of the fiber spectroscopic probe. The transmissive/reflective property of the optical mirror is wavelength-independent. Hence it can be used for all excitation/detection wavelengths.

In the foregoing specification, specific embodiments of the present invention have been described. However, one of ordinary skill in the art appreciates that various modifications and changes can be made without departing from the scope of the present invention as set forth in the claims below. The numerical values cited in the specific embodiment are illustrative rather than limiting. Accordingly, the specification and figures are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

What is claimed is:

1. A fiber spectroscopic probe mountable on a standard light microscope, said fiber spectroscopic probe comprising:
   an input optical fiber for delivering excitation light from an external light source;
   an adapter means detachable from said fiber spectroscopic probe, said adapter means being mountable directly above a nosepiece of the microscope for securing said fiber spectroscopic probe thereof to direct said excitation light through an objective lens of the microscope to a sample to excite a spectroscopic signal and collect said spectroscopic signal though said objective lens; and
   an output optical fiber for delivering said spectroscopic signal to an external spectrometer device for spectral analysis.

2. The fiber spectroscopic probe of claim 1, wherein said spectroscopic signal is a Raman scattering signal.

3. The fiber spectroscopic probe of claim 1, wherein said spectroscopic signal is a fluorescence or phosphorescence signal.

4. The fiber spectroscopic probe of claim 1, wherein said adapter means comprises a beam-combining/splitting member.

5. The fiber spectroscopic probe of claim 4, wherein said beam-combining/splitting member has a wavelength-dependent transmissive/reflective property.

6. The fiber spectroscopic probe of claim 1, wherein said adapter means comprises at least two switchable beam-combining/splitting members.

7. The fiber spectroscopic probe of claim 1, wherein said input optical fiber and output optical fiber are detachable.

8. The fiber spectroscopic probe of claim 1, wherein said input optical fiber and output optical fiber are selected from the group consisting of single mode optical fibers and multi-mode optical fibers.

9. The fiber spectroscopic probe of claim 1, further comprising a spatial pinhole in front of an output end of said input optical fiber.

10. The fiber spectroscopic probe of claim 1, further comprising an optical lens in front of an output end of said input optical fiber.

11. The fiber spectroscopic probe of claim 1, further comprising a spatial pinhole in front of an input end of said output optical fiber.

12. The fiber spectroscopic probe of claim 1, further comprising an optical lens in front of an input end of said output optical fiber.

13. The fiber spectroscopic probe of claim 1, further comprising an optical filter for separating a wavelength of said spectroscopic signal from a wavelength of said excitation light.

14. The fiber spectroscopic probe of claim 6, wherein said at least two switchable beam-combining/splitting members have different wavelength-dependent transmissive/reflective properties.

* * * * *